United States Patent
Malaczynski et al.

(10) Patent No.: US 10,329,989 B2
(45) Date of Patent: Jun. 25, 2019

(54) PARTICULATE MATTER DETECTION SYSTEM AND METHOD

(71) Applicant: DELPHI TECHNOLOGIES IP LIMITED, St. Michael (BB)

(72) Inventors: Gerard W. Malaczynski, Bloomfield Hills, MI (US); Gregory T. Roth, Davison, MI (US)

(73) Assignee: DELPHI TECHNOLOGIES IP LIMITED (BB)

( * ) Notice: Subject to any disclaimer, the term of this patent is extended or adjusted under 35 U.S.C. 154(b) by 88 days.

(21) Appl. No.: 15/266,008

(22) Filed: Sep. 15, 2016

(65) Prior Publication Data
US 2018/0073416 A1    Mar. 15, 2018

(51) Int. Cl.
| | |
|---|---|
| F01N 3/021 | (2006.01) |
| F01N 13/00 | (2010.01) |
| G01M 15/10 | (2006.01) |
| G01N 15/06 | (2006.01) |
| G01N 15/00 | (2006.01) |

(52) U.S. Cl.
CPC ........... *F01N 13/008* (2013.01); *F01N 3/021* (2013.01); *G01M 15/102* (2013.01); *G01N 15/0606* (2013.01); *G01N 15/0656* (2013.01); *F01N 2900/1606* (2013.01); *G01N 2015/0046* (2013.01)

(58) Field of Classification Search
USPC ....................................................... 73/23.33
See application file for complete search history.

(56) References Cited

U.S. PATENT DOCUMENTS

| | | | | |
|---|---|---|---|---|
| 5,049,255 | A * | 9/1991 | Wolfe | G01N 27/4062 204/424 |
| 6,321,531 | B1 * | 11/2001 | Caren | B01D 53/90 204/168 |
| 8,677,803 | B2 | 3/2014 | Hocken et al. | |
| 8,823,401 | B2 | 9/2014 | Roth et al. | |
| 2008/0000221 | A1 * | 1/2008 | Silvis | F01N 3/0814 60/286 |
| 2009/0230962 | A1 * | 9/2009 | White | G01N 24/08 324/317 |

(Continued)

FOREIGN PATENT DOCUMENTS

DE   102011086148 A1   5/2013

OTHER PUBLICATIONS

SAE International, 2012-01-0372, published Apr. 16, 2012, "Sensing of Particulate Matter for On-Board Diagnosis of Particulate Filters", Harry Husted, Gregory Roth, Scott Nelson, Lary Hocken, Gary Fulks, David Racine; Delphi Automotive Systems, LLC.

*Primary Examiner* — Peter J Macchiarolo
*Assistant Examiner* — Mohammed E Keramet-Amircolai
(74) *Attorney, Agent, or Firm* — Joshua M. Haines

(57) ABSTRACT

A method of quantifying a particulate matter in an exhaust stream includes the steps of accumulating a particulate matter on a sensor. The sensor provides a signal that varies based upon an amount of the particulate on the sensor. The sensor includes a measurement cycle that includes a deadband zone, followed by an active zone, which is followed by a regeneration zone. The particulate matter is calculated after an end of the deadband zone is reached and prior to an end of the measurement cycle.

16 Claims, 13 Drawing Sheets

(56) References Cited

U.S. PATENT DOCUMENTS

| | | | |
|---|---|---|---|
| 2009/0301058 A1* | 12/2009 | Boehler | G01N 15/0656 60/276 |
| 2011/0120088 A1* | 5/2011 | George | F01N 3/021 60/274 |
| 2011/0131954 A1* | 6/2011 | Parnin | F01N 3/027 60/276 |
| 2013/0233051 A1* | 9/2013 | Harshbarger | F01N 11/00 73/23.31 |
| 2014/0345362 A1* | 11/2014 | Lee | G01N 15/0656 73/23.31 |
| 2015/0114339 A1* | 4/2015 | Sellnau | F02N 19/04 123/294 |
| 2015/0211429 A1* | 7/2015 | Hocken | F02D 41/029 324/601 |
| 2016/0131013 A1* | 5/2016 | Yi | F01N 13/08 60/274 |
| 2016/0201537 A1* | 7/2016 | Ettireddy | B01D 53/9418 60/297 |
| 2016/0265413 A1* | 9/2016 | Willimowski | F01N 11/005 |
| 2017/0037754 A1* | 2/2017 | Shade | F01N 13/008 |
| 2017/0067813 A1* | 3/2017 | Zhang | G01M 15/102 |

\* cited by examiner

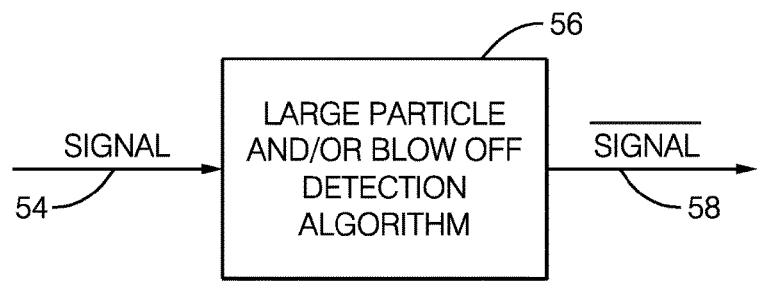
FIG. 5
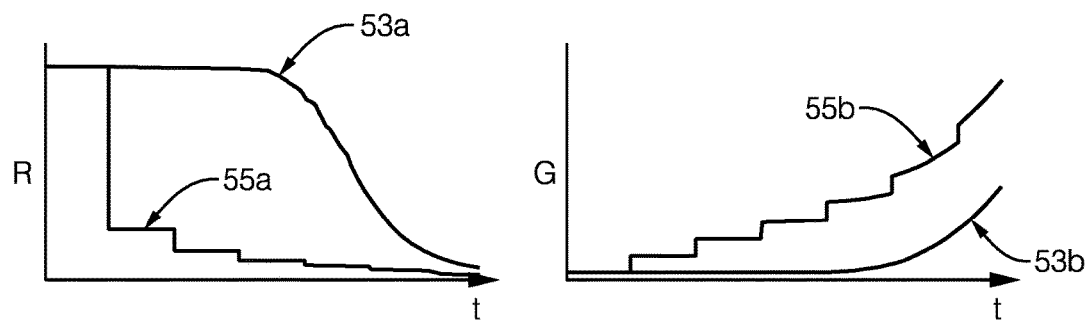
FIG. 6A
FIG. 7A
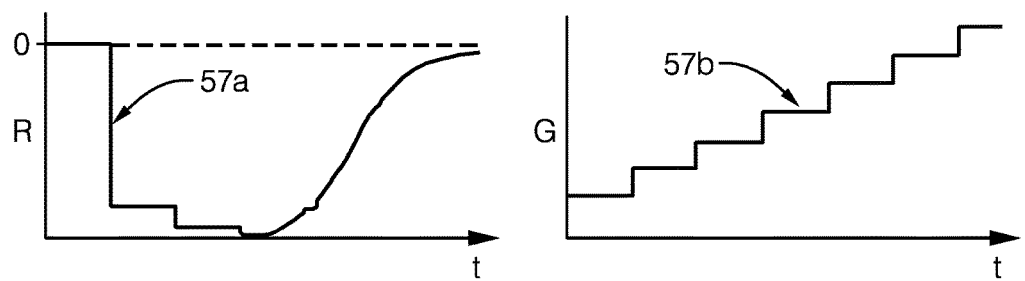
FIG. 6B
FIG. 7B

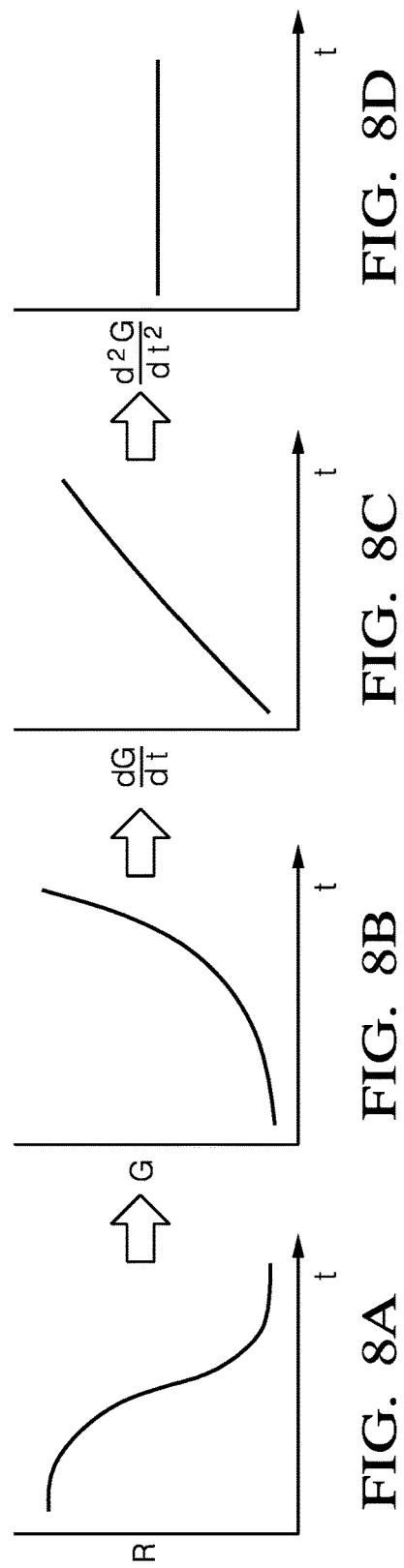

PARTICULATE MATTER DETECTION SYSTEM AND METHOD

BACKGROUND

This disclosure relates to system and method of detecting particulate matter throughout a particulate matter sensor measurement cycle.

Rich combustion conditions, such as those which occur in diffusion flame processes that are present in diesel engines and other internal combustion engines, produce particulate matter, which is carried in its exhaust stream. Particulate matter emissions are typically limited by emissions regulations and it is common for modern diesel engines to be equipped with a particulate filter. As part of the emissions regulations, diagnosis of the particulate filter is mandated and the use of a particulate matter sensor is one such diagnostic system. Thus, it is desirable to accurately measure particulate matter real-time in vehicles to ensure that the engine and particulate filter are operating in compliance with government regulations. It is also desirable to measure particulate matter using emissions testing equipment during engine development on a dynamometer, for example.

One type of particulate matter sensor includes electrodes that are closely spaced on an electrically non-conductive substrate. As particulate matter accumulates between the electrodes, the sensor's electric resistance decreases as the initially non-conductive substrate surface between electrodes becomes gradually more electrically conductive due to the deposited particulate matter (PM) or soot, which is indicative of the amount of particulate matter in the sensed exhaust pipe, either directly produced by the combustion process or its remnants escaping the action of the particulate filter.

During the measurement cycle, a typical particulate matter sensor only measures soot during an active zone. Once a predetermined threshold has been reached, which corresponds to the sensor being saturated with soot to a predefined extent, the sensor undergoes regeneration to prepare the sensor to again measure the accumulation of soot. Subsequent to regeneration and prior to reaching the active zone, the sensor has a deadband zone in which there has been no measurement of soot due to the very small change in conductance within the sensor during the initial soot deposition period. Instead, a sensor measurement controller utilizes the sensor response time (the time span between the end of sensor regeneration to the subsequent start of sensor regeneration) as the output parameter indicating the level of soot in the exhaust stream. The engine ECM receives this time interval, compares this time interval to a calibration table, and calculates a corresponding pass/fail diagnostic determination.

This particulate matter measurement method has several drawbacks including a long response time (possibly tens or hundreds of minutes for low soot level conditions), provides only a time-integrated output with no real-time response, and provides no direct measure of soot level, only a measure of time interval which requires the customer to interpret the results via a calibration table to compensate for exhaust velocity and flow area. As particulate matter begin to deposit, they are sparse and their deposition causes undetectable change in sensor resistance due, in part, to the presence of a bias resistor in the sensor's circuit (used for diagnosing the sensor itself), which causes the deadband zone. Previously, deadband time had been ignored by the ECM and was considered an undesirable characteristic of the sensor design.

Diesel particulate filter diagnostic decisions, for example, must be made during one Federal Test Procedure drive cycle, which is approximately 11 miles and 31 minutes in length.

Additionally, experimentally observed step-like unusual changes in the measured particulate matter deposit resistance are commonly attributed to either occasional bombardment of the sensor surface with particles much larger than the typical size within the particles' size distribution, or losses of already-deposited particle mass due to blow-offs. This dramatic alteration of particulate matter resistance gradient measured in the time domain corrupts the particulate matter concentration assessment algorithm which may be based on the measure of the cycle time, i.e., time markers representing arbitrarily selected sensor resistances indicating the start of sensing cycle and its end. These error effects are explained in, for example, "Sensing of Particulate Matter for On-Board Diagnosis of Particulate Filters", H. Husted et al, SAE Int. J. Engines 5(2) (2012).

There is a need to obtain and interpret accurate readings from the particulate matter sensor as often as possible and quickly calculate particulate matter mass, concentration and flux based on sensor output.

SUMMARY

In one exemplary embodiment, a method of quantifying a particulate matter in an exhaust stream includes the steps of accumulating a particulate matter on a sensor. The sensor provides a signal that varies based upon an amount of the particulate on the sensor. The sensor includes a measurement cycle that includes a deadband zone, followed by an active zone, which is followed by a regeneration zone. The particulate matter is calculated after an end of the deadband zone is reached and prior to an end of the measurement cycle.

In a further embodiment of the above, the particulate matter calculating step includes determining at least one of a particulate matter mass, a particulate matter flux, and a particulate matter concentration.

In a further embodiment of any of the above, the particulate matter calculating step includes determining at least one of an average amount and an instantaneous amount of the at least one of the particulate matter mass, the particulate matter flux, and the particulate matter concentration.

In a further embodiment of any of the above, the instantaneous amount of the at least one of the particulate matter mass, the particulate matter flux, and the particulate matter concentration is calculated using a second differential of conductance from the signal.

In a further embodiment of any of the above, the particulate matter calculating step is performed at an end of the active zone.

In a further embodiment of any of the above, the particulate matter calculating step is performed within the active zone.

In a further embodiment of any of the above, the particulate matter calculating step is performed when the signal reaches a desired resistance.

In a further embodiment of any of the above, the method includes the step of reporting the calculated particulate matter if the measurement cycle is terminated prematurely.

In a further embodiment of any of the above, the method includes a step of calculating a particulate matter in the deadband zone based upon the signal reaching a threshold resistance and a deadband zone total time at which the threshold resistance is reached from an end of the regeneration zone. The method also includes is the step of summing a particulate matter from the deadband zone and the active zone to determine a total accumulated particulate matter during the measurement cycle.

In a further embodiment of any of the above, the method includes an exhaust system fluidly connected to an engine. The exhaust system defines the exhaust stream. The sensor includes a heater and is provided in the exhaust system. The method includes the step of energizing the heater in the regeneration zone.

In a further embodiment of any of the above, the method includes the step of calculating a cumulative particulate matter during a vehicle drive cycle.

In another exemplary embodiment, a method of quantifying a particulate matter in an exhaust stream includes the steps of accumulating a particulate matter on a sensor. The sensor provides a signal that varies based upon an amount of the particulate on the sensor. The sensor includes a measurement cycle that includes a deadband zone, followed by an active zone, which is followed by a regeneration zone. The particulate matter is calculated in the deadband zone based upon the signal reaching a threshold resistance and a deadband zone total time at which the threshold resistance is reached from an end of the regeneration zone.

In a further embodiment of any of the above, the particulate matter calculating step includes determining at least one of an average particulate matter mass, an average particulate matter flux, and an average particulate matter concentration.

In a further embodiment of any of the above, the method includes outputting a diesel particulate filter status message based upon the deadband zone total time exceeding a threshold.

In another exemplary embodiment, a system includes an exhaust system fluidly configured to define an exhaust stream. A sensor is arranged in the exhaust system and is configured to be exposed to the exhaust stream and accumulate a particulate matter on the sensor. The sensor provides a signal that varies based upon an amount of the particulate matter on the sensor. The sensor is configured to provide a measurement cycle that includes a deadband zone, followed by an active zone, which is followed by a regeneration zone. A control system is in communication with the sensor. The control system includes a controller configured to calculate at least one of the particulate matter after an end of the deadband zone is reached and prior to an end of the measurement cycle and the particulate matter in the deadband zone based upon the signal reaching a threshold resistance and a deadband zone total time at which the threshold resistance is reached from an end of the regeneration zone.

In a further embodiment of any of the above, the controller is configured to determine at least one of a particulate matter mass, a particulate matter flux, and a particulate matter concentration when calculating the particulate matter.

In a further embodiment of any of the above, the controller is configured to report the calculated particulate matter if the measurement cycle is terminated prematurely.

In a further embodiment of any of the above, an exhaust system is fluidly connected to an engine. The exhaust system defines the exhaust stream. The sensor includes a heater and is provided in the exhaust system. The controller is configured to energize the heater in the regeneration zone in response to the calculated particulate matter.

In a further embodiment of any of the above, the controller is configured to calculate a cumulative particulate matter during a vehicle drive cycle.

BRIEF DESCRIPTION OF THE DRAWINGS

The disclosure can be further understood by reference to the following detailed description when considered in connection with the accompanying drawings wherein:

FIG. 5 schematically depicts a signal correction to remove an error effect based upon an anomaly relating to particulate matter accumulation on the sensor.

FIG. 6A illustrates a "clean" signal and a "corrupted" signal in resistance versus time.

FIG. 6B illustrates the difference between the "normal," i.e., not affected by large particles strikes and/or blow-offs, signal and the "corrupted" signal shown in FIG. 6A.

FIG. 7A illustrates a "normal" signal and a "corrupted" signal in conductance versus time for the resistance shown in FIG. 6A.

FIG. 7B illustrates the difference between the "normal" conductance signal and the "corrupted" sensor's conductance signal shown in FIG. 7A.

FIGS. 8A, 8B, 8C and 8D respectively illustrate a resistance signal, a conductance signal, and a first derivative of the conductance signal in the case of constant soot concentration, constant sensor surface temperature, constant exhaust gas velocity, and a second derivative of the conductance signal.

The embodiments, examples and alternatives of the preceding paragraphs, the claims, or the following description and drawings, including any of their various aspects or respective individual features, may be taken independently or in any combination. Features described in connection with one embodiment are applicable to all embodiments, unless such features are incompatible.

DETAILED DESCRIPTION

Figure 1:
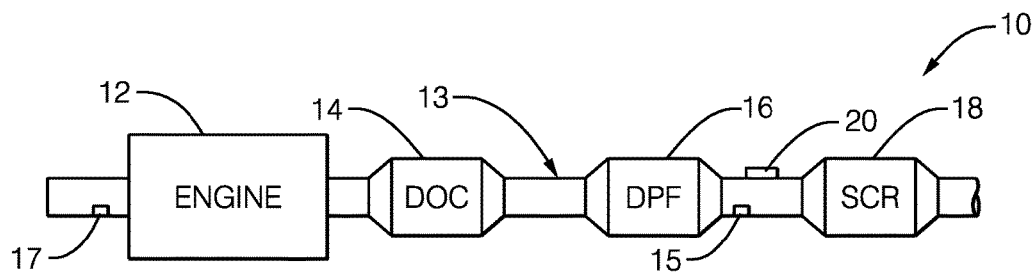
FIG. 1 is a schematic view of an exemplary powertrain system.

An example vehicle powertrain system 10 is shown in FIG. 1. The system 10 includes an engine 12, which in this non-limiting exemplary embodiment is a diesel engine, fluidly connected to an exhaust system 13 that includes a diesel oxidation catalyst (DOC) 14 and a diesel particulate filter (DPF) 16. A selective catalyst reduction (SCR) catalyst, such as those used in conjunction with a urea injection system, is arranged downstream from the DPF 16.

A particulate matter (PM, also referred to as "soot") sensor 20 is arranged in the exhaust system 13, typically in proximity to the DPF 16, although it should be understood that the PM sensor 20 may be located elsewhere. The PM sensor 20 is configured to be exposed to the exhaust stream and accumulate PM on its internal sensing element. The PM sensor 20 provides a resistance signal that varies based upon an amount of the PM on the sensor.

An exhaust gas temperature sensor 15 is arranged in the exhaust stream in proximity to the PM sensor 20 to provide an exhaust temperature (T) signal. An air flow sensor 17 may placed in the intake to the engine or an estimator may be used to provide exhaust mass flow rate and velocity. These signals can be used for measurement compensation and converting the measured PM values to various unit formats. Alternatively, instead of providing gas temperature sensor 15, the PM sensor can offer the temperature measurement if a temperature sensing element is integrated with the sensor structure.

Figure 2:
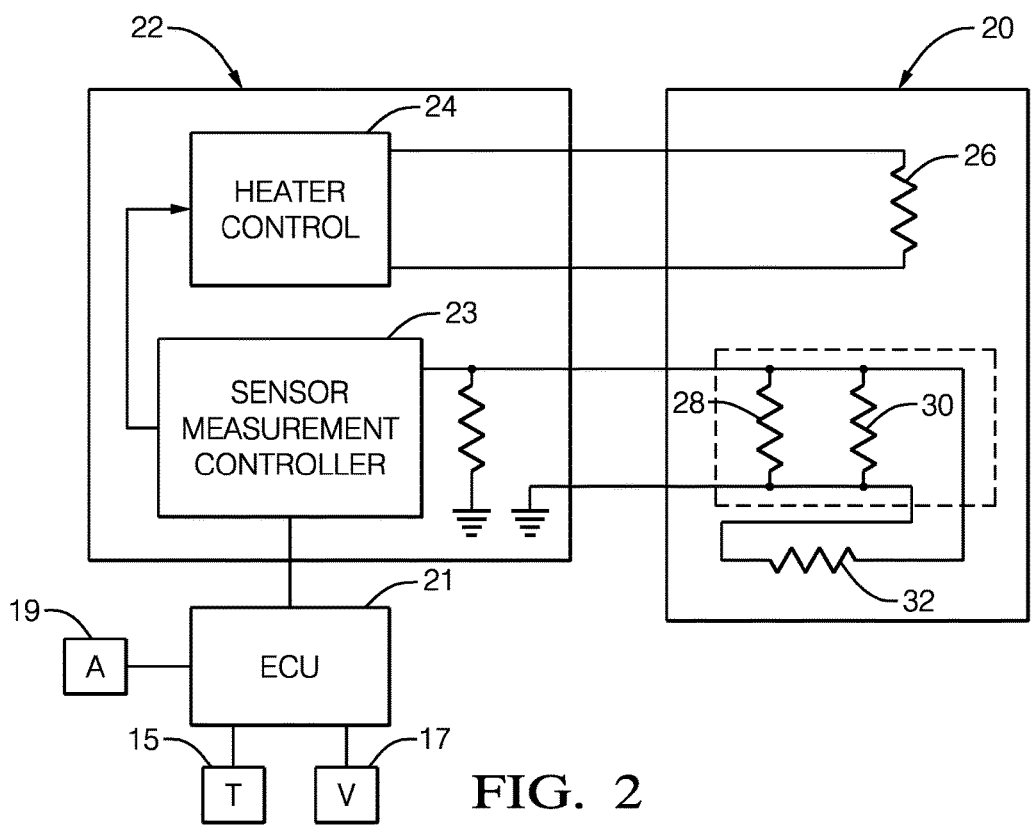
FIG. 2 is a circuit schematic for a particulate matter sensor and its controller.
Figure 3:
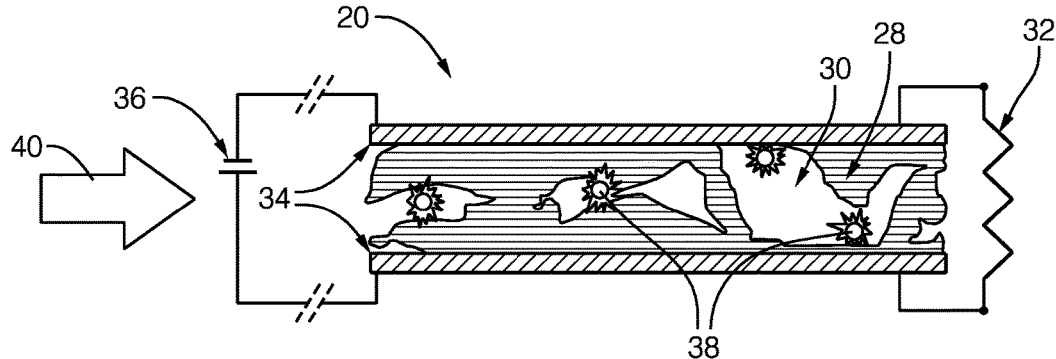
FIG. 3 is schematic of the particulate matter sensor during a particulate matter particle strike.

Referring to FIG. 2, a control system 21, such as an engine control unit (ECU), is in communication with the PM sensor controller 22 which includes a sensor measurement controller 23 that controls a sensing cycle (e.g., shown in FIGS. 4A and 4B) for the sensor based upon its resistance. The ECU 21 is in communication with reference data 19 for the cross-sectional area (A) of the exhaust passage as well as the temperature sensor 15 and air flow sensor 17. In one type of PM sensor 20, soot, substrate and bias resistor 28, 30, 32 are connected in parallel with one another. The substrate resistor 30 represents the resistance of a "clean", i.e. not contaminated with the soot deposit, sensor 20, and the bias resistor 32 is used for diagnosing the sensor 20. The substrate resistance is very large relative to the other resistances. The soot-representing resistor 28 is provided by a pair of spaced apart electrodes 34 such that when no PM is present, the electrodes provide an open circuit in parallel with bias resistor 32 and substrate resistance 30 with a power source 36, as shown in FIG. 3. As PM 38 in the exhaust stream 40 deposits on the sensor surface between electrodes 34 the soot deposit resistance in parallel with the bias resistor provide gradually decreasing effective electrical resistance (increasing effective electrical conductance) of the sensor measured by the system electronics.

After a predetermined sensor electrical conductance is reached, which represents a maximum desired soot accumulation at the sensor surface, there is a need for the removal of the soot as further soot accumulation might lead to a poor reliability of the data interpretation and carry a risk of ineffective soot oxidation (cleaning) procedure with the heater 26 integrated with the sensor. Returning to FIG. 2, to begin the sensing cycle again, the sensor measurement controller 23 commands a heater module 24 to activate a sensor heater 26 in the PM sensor 20, which oxidizes the accumulated PM and regenerates the sensor, typically in response to a threshold total accumulated particulate matter being reached.

The PM sensor controller 22 can be part of an onboard vehicle PM sensing system or part of an emissions testing system suitable for use in, for example, a test laboratory during engine testing and calibration. In the example of an emissions test system, the PM sensor controller 22 may output particulate matter data to a laboratory data acquisition system during the engine test procedure.

Figure 4A:
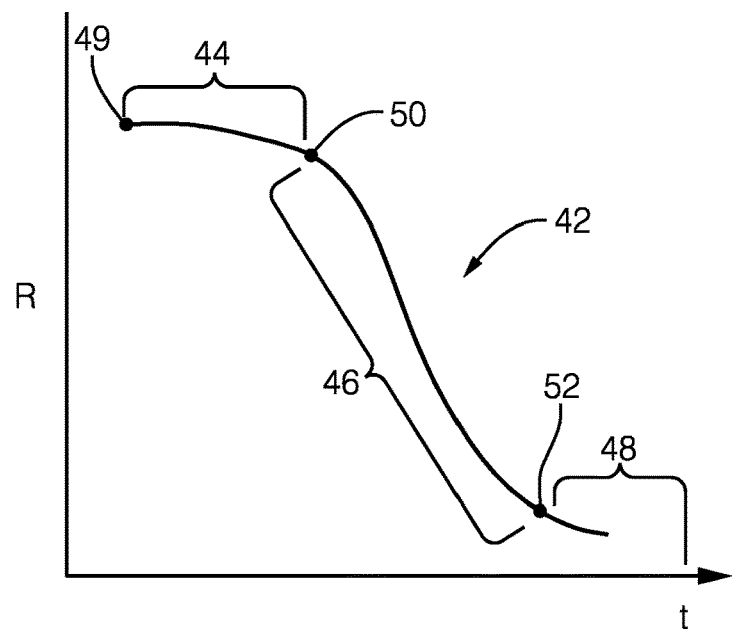
FIG. 4A is a graph of a sensing cycle based upon resistance versus time.
Figure 4B:
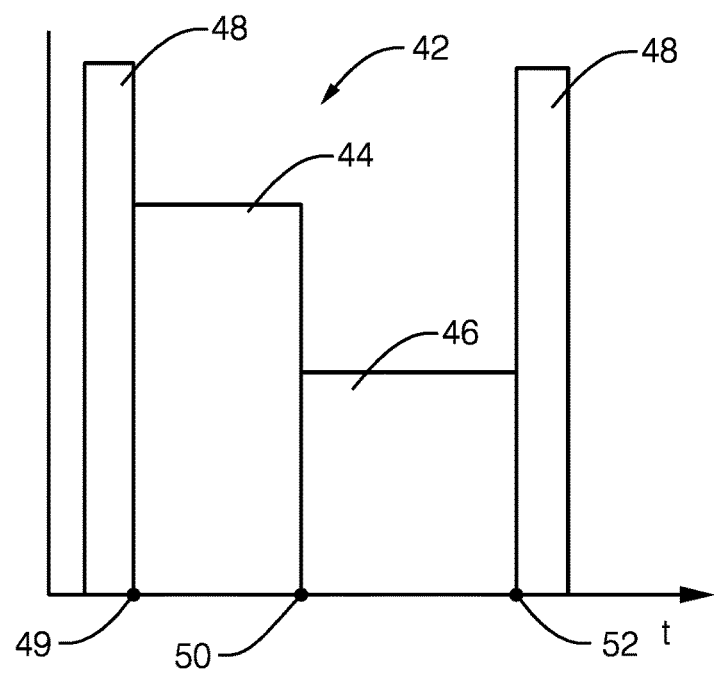
FIG. 4B is a schematic illustrating various zones during the sensing cycle.

One example sensing cycle 42 is shown in FIGS. 4A and 4B. Referring to FIG. 4B, the sensing cycle 42 has a deadband zone 44, an active zone 46 and a regeneration zone 48. As shown in FIG. 4A, prior to the starting point 50 of the active zone 46, the resistance of the sensor 20 is relatively flat and unchanged since sufficient PM has not yet accumulated in the sensor 20 to bridge the electrodes 34. In this deadband zone, from the end of regeneration 49 to the starting point 50, no meaningful data is typically gathered concerning PM accumulation. The deadband zone exit point 50 is defined as a first point along the measured electric conductance trace, which can be reliably identified and is sufficiently free of stochastic noise. In one example, the sensor resistance at the end of regeneration 49 is around 10 MΩ, and the sensor resistance at the starting point 50 is around 8 MΩ. From the starting point 50 to a stopping point 52, which may be around 1 MΩ, the resistance steadily decreases, which is indicative of PM accumulation.

Traditionally, soot measurements where only made by the PM sensor 20 at the conclusion of the active zone 52, ignoring the deadband zone 44 and the active zone itself 42. The response time (from the end of regeneration 49 to the end of active zone 52) is traditionally the measure used to assess cumulative soot mass. Between the stopping point 52 (onset of regeneration) and conclusion of deadband (point 50, FIG. 4A) preceded by regeneration (48 in FIG. 4B), no meaningful data can be directly gathered as the resistance measurement during regeneration (as commanded by the sensor measurement controller 23) changes abruptly in the response to soot oxidation and after, for the duration of the deadband interval 44, remains generally unchanged, since the sensor experiences an early soot accumulation period dominated by the bias resistor.

The sensor measurement controller 23 is configured to identify an error effect based upon an anomaly relating to the accumulation of the particulate matter. One such anomaly is due to large particle (LP) strikes on the sensor 20. It can be appreciated that once the size of a large particle approaches the width of the electrodes 34, the deposition of this large particle across the electrodes results in a step-like decay of the measured sensor resistance. This step change in resistance is then erroneously interpreted as spikes in soot flux and leads to erroneous interpretation of the measured time elapsed between zone markers (i.e., starting and stopping points 50, 52) representing calibrated sensor resistance thresholds. Thus, in addition to obtaining an inaccurate total accumulated PM, the sensing cycle will be unnecessarily shortened, which results in proportionally more time in the deadband zone 44 and the regeneration zone 48 wherein PM data is not collected. Noticeably, same size large particle strikes result in gradually decreasing step size in the affected sensor resistance trace as time/deposition of soot progresses. The reason for this non-linearity in the sensor signal response to same size large particle strike lies in the fact that the sensor resistance is the combination of the three resistors 28, 30, 32 connected in parallel, and resistance representing gradually increasing soot deposit.

Conversely, a particle blow-off condition creates another anomaly in which a step-like increase of the measured sensor resistance occurs due to particles becoming dislodged from between the electrodes 34. An additional condition in which a large particle or agglomerate makes intermittent contact with the sensor electrodes 34 is sensed as a blow-off condition that alternates with large particle strikes in a repeated manner is termed "an unstable soot deposit condition." This surface instability where the resistance signal suddenly increases and then decreases again in a repeating pattern is undesirable for PM flux measurement. The sensor measurement controller 23 initiates a sensor regeneration when an unstable soot deposit condition is detected as no meaningful PM accumulation data can be gathered (cycle abort procedure).

Figure 9A:
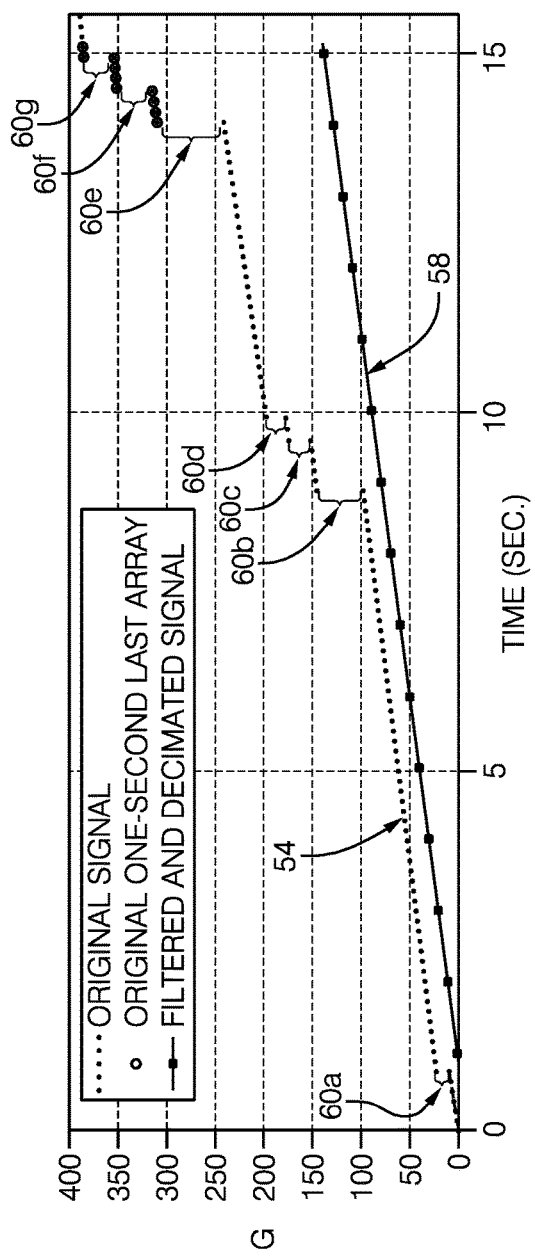
FIG. 9A illustrates a corrupted original conductance signal and a reconstructed conductance signal after conforming erroneous data points, identified by analyzing the first differential of the corrupted conductance signal, which is shown in FIG. 9B.
Figure 9B:
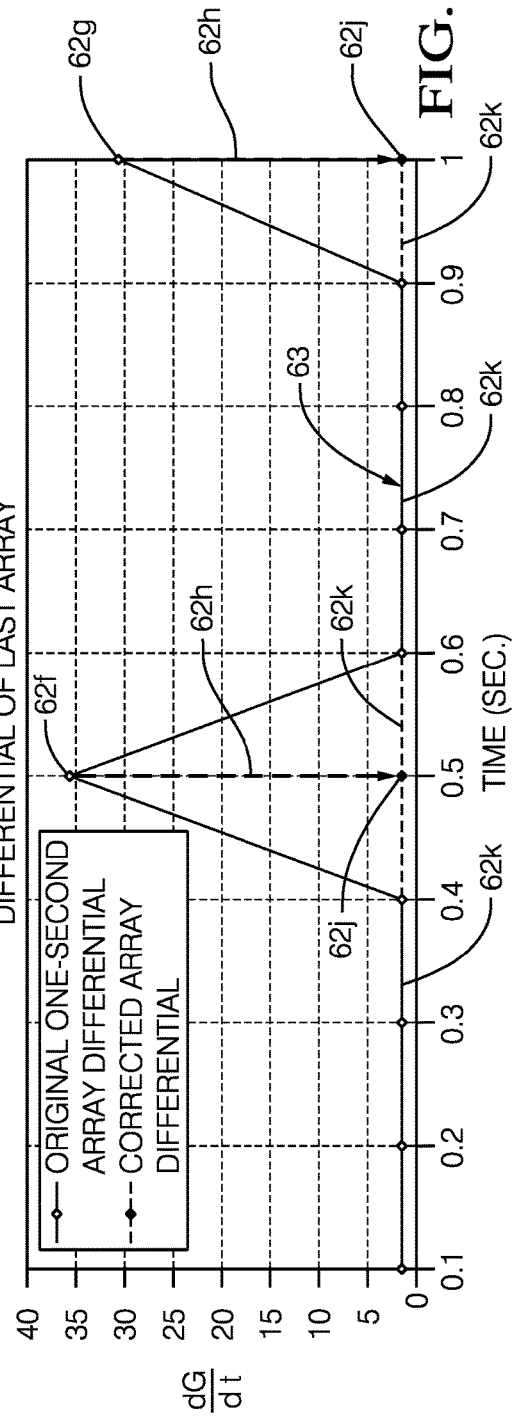
FIG. 9B illustrates the first differential of the corrupted conductance signal with the erroneous data points, and a corrected first differential of the corrupted conductance signal after the erroneous data points have been conformed.

FIG. 5 schematically depicts a signal correction of a corrupted signal 54 to remove the above error effects 56 based upon an anomaly, such as large particle strikes and/or blow-offs that occur during particulate matter accumulation on the sensor. A reconstructed signal 58 is generated with the error effects removed. An example of signal correction is depicted in FIGS. 9A and 9B, for example.

FIG. 6A illustrates a "normal" signal 53*a* and a large particles strike-"corrupted" signal 55*a* in resistance versus time for an identical, repetitive large particle strike condition. FIG. 6B illustrates the mathematical difference between the "normal" signal and the "corrupted" signal shown in FIG. 6A ("corrupted" minus "normal"), which highlights non-linearity induced by algorithms operating in the electrical resistance domain when processing the PM sensor signal. Thus, the sensor measurement controller 23 is configured to convert the resistance signal to a conductance signal, which provides a signal shape that is much easier to process—even when corrupted. FIG. 7A illustrates a "normal" signal and a "corrupted" signal in the conductance domain versus time, which is generally parabolic in shape with anomalies generated by identical large particle strikes inducing well-behaved step changes. FIG. 7B illustrates the mathematical difference between the "normal" signal and the "corrupted" signal shown in FIG. 7A ("corrupted" minus "normal"), which provides a more manageable, uniform step response to large particle strikes.

Thus, the disclosed correction method converts the resistance signal (FIG. 8A) to the conductance signal (FIG. 8B), which is a generally parabolic shape for engine steady-state conditions (constant soot flux, constant sensor surface temperature, and constant exhaust velocity). The first differential of the conductance is calculated (FIG. 8C), which provides a generally linear signal. The error effect in the first differential of conductance will manifest itself as erroneous data points that depart from the otherwise generally linear signal. The large particle condition will manifest itself as a sudden short duration increase in the first differential of the conductance (sudden decrease in resistance signal). Conversely, the blow-off condition will manifest itself as a sudden short duration decrease in the first differential of the conductance (sudden increase in resistance signal). Once the abnormalities are removed and the conductance signal of the sensor reconstructed without the effect of large particle strikes and/or blow-offs the second differential of conductance (FIG. 8D) is calculated and provides a measure of soot flux.

The sensor measurement controller 23 is configured to determine a total accumulated particulate matter while accounting for the error effect of large particles and/or blow-offs. Referring to FIGS. 9A and 9B, a corrupted signal due to large particle strikes is shown, which results in erroneous data points that are dissimilar to the trend provided by the other data points. A differential of the conductance signal is calculated at a first sampling frequency. Consecutive differentials are compared to identify an erroneous differential in an abnormal signal based upon an anomaly relating to the accumulation of the particulate matter. In the example, the first sampling frequency includes a first sample point from a previous array, and the second sampling frequency includes decimated samples from the corrected array. The erroneous differential in the abnormal signal is reconstructed to produce a corrected, decimated conductance signal at a second sampling frequency that is lower than the first sampling frequency.

In the example, the conductance signal is sampled at, for example, 100 ms intervals (FIG. 9A), and after replacement of conductance differential array elements (FIG. 9B) violating the threshold limits for large particles and blow-offs, the conductance array is reconstructed at a fraction of the original sampling frequency, in the illustrated case at one second intervals (FIG. 9A, dots linked by solid line). Of course, other time intervals can be used, if desired. The data in FIG. 9B is for a small time period and therefore does not reflect the second order curvature that is present in the full cycle data set.

The large particle strikes are indicated by the increases 60*a*-60*g*, resulting in a corrupted signal 54. FIG. 9B more closely examines the first differential of the signal at 60*f* and 60*g* that respectively correspond to the increases 60*f* and 60*g* with anomalies evident in the differential at 62*f* and 62*g* respectively. The controller 22 identifies these erroneous data points by sampling the conductance signal at a high rate (in this example 100 ms), creating an array of 11 closely spaced samples, for example. This array is then differentiated, which facilitates identification of anomalies by comparison of adjacent sample amplitudes. The normal operation of the sensor produces a relatively stable differential array with small fluctuations. Large deviations (above a threshold level) are identified anomalies (62*f* and 62*g*), which are the subject of correction. The algorithm then modifies the identified points by leveling the differential (62*h*) to the normal level in that array, resulting in the conformed differentials 62*j*. The conformed signal 62*k* is then used for reconstruction of sensor conductance 58 (generally straight line in FIG. 9A) in new sampling domain (in our example 1 second).

For large particle conditions corrected in the manner above, an accurate total accumulated particulate matter of normal size distribution is represented by the corrected conductance trace. The large particle strike condition causes a sudden decrease in the resistance signal (or increase in conductance). However, for large particle conditions, the conformed erroneous data points represent removal of the particle from the ongoing measurement. To maintain overall accuracy, the large particles are accounted for by calculating the effective size of the large particle based on the size of the disturbance and then added to the normal particulate accumulation mass to provide an accurate total accumulated particulate matter.

The formulas for detecting the anomalies may be programmed using the syntax described below. The differential between two subsequent readings is not expected be larger than a certain pre-defined level (called threshold(1)) under normal PM accumulation if compared to the prior measured differential, otherwise the data point is flagged as being a large particle anomaly.

In general, an input array of differential d may have size length(d) which is indicated in the formulation below and is shown as an input array of ten elements in FIG. 9B, which illustrates how the 100 ms sampled conductance differential signal is transformed 62h to reconstruct the error-free (large particles-free) conductance differential 62j and then the decimated conductance signal 58 in FIG. 9A in 1 second sampling domain (correction followed by decimation).

The syntax for large particles detection may look as follows:

```
for m=1:length(d)-1
    if (d(m+1)-d(m))>threshold(1)
        flag1=flag1+1;
        a1=a1+d(m+1)-d(m);
        d(m+1)=d(m);
    end
end
```

This formula provides for correction of excessive differential to the previous one in the array, which relies upon overlapping one of the ten element arrays of signal differentials by one sample from the previous array to allow for correction when the first element in the array violates the threshold. The last element of the previous array is provided only to compare to the first element of new array and "level" (if correction is needed) the first element in the new array with the last element of the previous array. Alternatively, if the desired correction is expected to "level" the output to an average of a few previous readings, then the overlap in the array needs to be adjusted accordingly.

If the correction formula is expanded to more than one element overlap, the sizes of the arrays, number of elements fed back with 1 second delay, and number of elements grounded at the output must be adjusted accordingly.

Similarly, with a different threshold level (threshold(2)) calibration assigned for the detection of blow-offs, the corresponding portion of the syntax embedded into the module may look as follows:

```
for m=1:length(d)-1
    if d(m+1)<-threshold(2)
        flag2=flag2-1;
        a2=a2+d(m+1)-d(m);
        d(m+1)=d(m);
    end
end
```

A particulate blow-off condition on the sensor causes a sudden increase in the resistance signal (or decrease in conductance). The reconstructing step includes increasing the erroneous conductance differential to a level represented by a previous, not questionable or already corrected element, or mean or median of previous elements, in the pre-defined in length array or earlier array if the questionable element is first in a currently processed array.

The subroutines for large particles and blow-off detections follow each other in the algorithm and are executed only if the violation of the relevant threshold level(s) is/are sensed. This action facilitates counting independently the occurrences of large particle (flag1), blow-off (flag2) conditions, and adds up independently the differential amplitudes indicative of large particle and blow-off events (a1 and a2), which provide information on the severity of the misbehavior. Also, when the large particle differential a1 is scaled (calibrated) it provides additional information regarding cumulative mass of the deposit and/or size of the large particles involved. Sizing of the differential a2 can be used to assess severity of the blow-off, thus is useful in the interpretation of the phenomena, but is not used when monitoring total cumulative deposit, as the blow-off-corrected conductivity signal inherently nullifies the signal corruption induced by blow-offs. The core output of the filter, however, is an array of corrected conductance signal differentials which is subsequently used to reconstruct the input conductance signal in the new sampling domain of 1 second, for example.

The correction procedure starts at the conclusion of the sensor regeneration 48 and ends at the conclusion of active zone 46 and the onset of next regeneration. The reading of the sensor resistance/conductance, when compared to calibrated maximum conductance marking the upper limit of soot accumulation at the sensor's surface (FIG. 4A, point 52) provides the trigger signal for the sensor regeneration. The reading of the sensor conductance at the onset of the new cycle is represented by the conductance of the clean (not contaminated with soot) substrate in parallel with the bias resistor.

While large particle strikes are expected to be rare, unusual events, it is expected that minute blow-offs occur frequently. If all negative differentials of the conductance were flagged as blow-offs, electronic noise would be misinterpreted as minute blow-off and, therefore, create erroneous corrections. Consequently, the threshold level for blow-offs is set at the level ignoring the system-specific electronic noise. The blow-off threshold level, threshold(2), can be experimentally selected to filter out this "background" effect so that the reconstructing step is performed above the minimum blow-off detection level. Similarly, every particle strike results in a minute increase of the conductance. However, only very large particle strike events require the filter action leading to the correction of the conductance signal. Consequently, the threshold level, threshold(1), which violation initiates the correction for large particle strike is set differently and its value can be roughly estimated using a simulation-based-calibration modeling technique.

Figure 10:
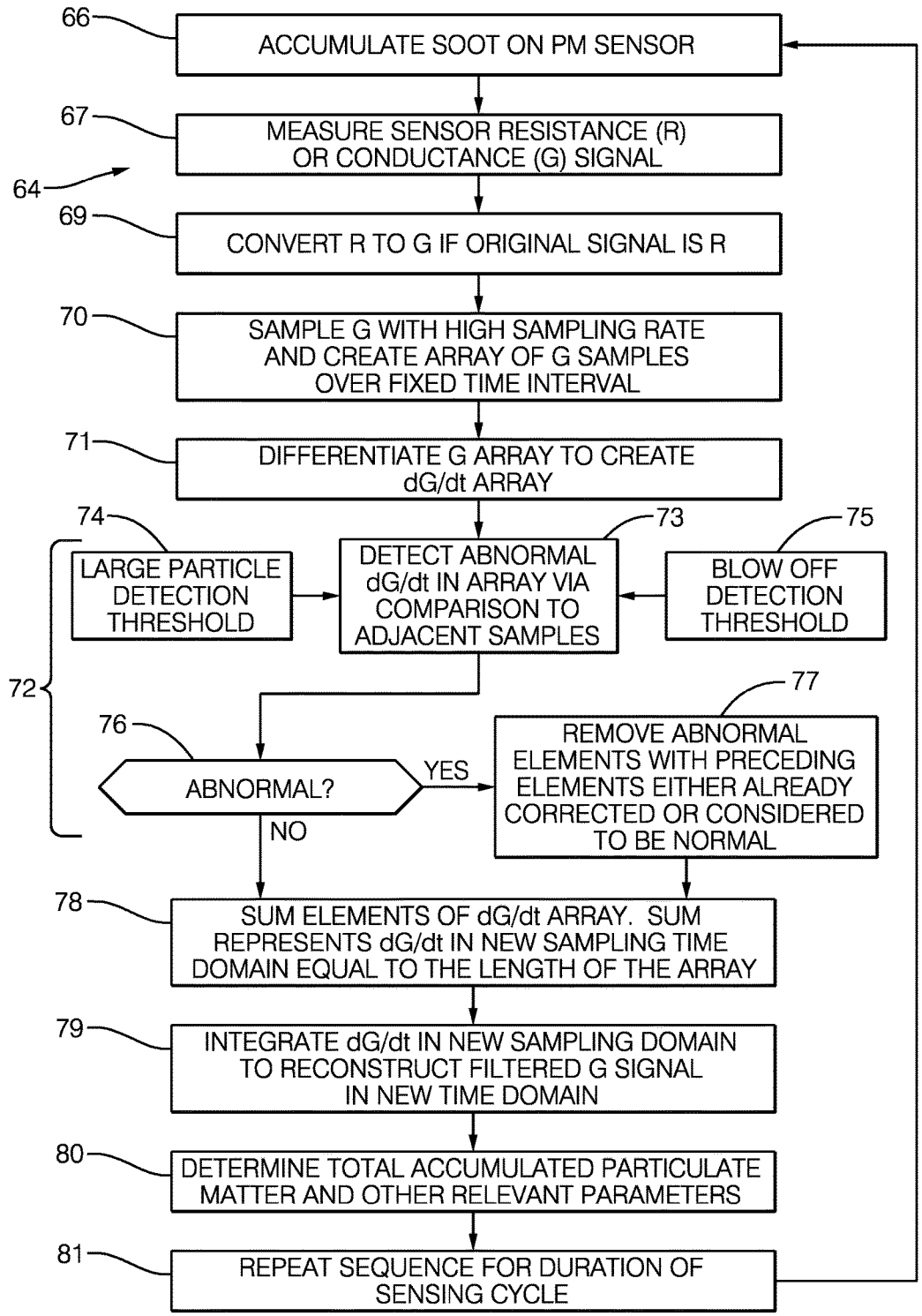
FIG. 10 is a flow chart depicting an example method of correcting a particulate matter sensor signal.

In summary, one example method of PM measurement and correction is illustrated in the flowchart shown in FIG. 10. Soot is accumulated on the PM sensor 20, as indicated at block 66. The amount of PM is output as a resistance signal (and later converted to conductance in block 69), or as a conductance signal, as indicated in block 67. Conductance is sampled at a relatively high rate to create a conductance array over a fixed time interval (block 70), and a first differential array of the conductance is created (block 71).

Anomalies are detected in an abnormal first differential signal of the conductance by making comparisons to adjacent samples, as indicated by block 73. Using large particle strike and blow-off detection thresholds (blocks 74 and 75), undesired deviations from the adjacent samples are identified, and if sufficiently abnormal (block 76), are removed with respect to normal sample points to remove the error effects of the anomaly (block 77). The sample points in the revised array of the first differential of conductance are then summed in a new sampling time domain equal to the length of the array (block 78), and this new sampling time domain can then be reconstructed to provide a filtered conductance signal that is error-free with respect to the anomaly (block 79). The total accumulated PM and other relevant parameters can then be determined from this corrected conductance signal (block 80). The sequence can be repeated throughout the measurement cycle (block 81) to provide a continuous output of total accumulated PM during engine operation in a vehicle or an engine dynamometer.

Figure 10A:
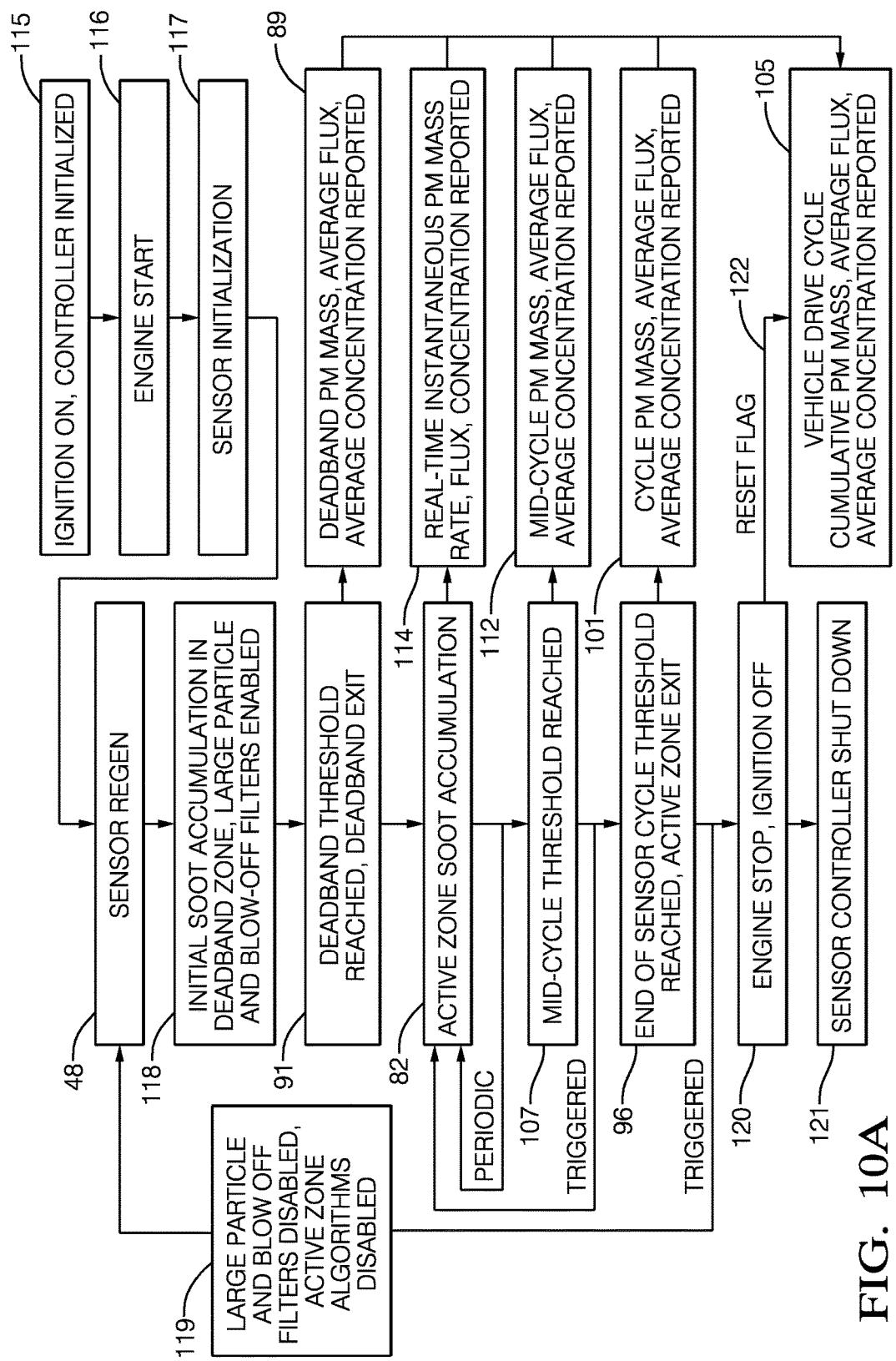
FIG. 10A is a flow chart depicting overall sensor and sensor controller operation.

FIG. 10A provides the overall flowchart of sensor and sensor controller algorithms. Further detail of each block is contained below. When vehicle ignition is turned on, the PM sensor controller initializes 115. Once the engine is started 116, the sensor initializes 117, regenerates 48 if needed, and begins soot accumulation 118. The sensor cycle continues in the deadband zone 118 until the deadband threshold is reached 91, at which time the deadband PM measurements are reported 89. The sensor continues into the active zone 82 and periodically reports instantaneous PM information 114. When mid-cycle thresholds are reached 107, mid-cycle PM parameters are reported 112 and the PM accumulation and real-time instantaneous reporting continues. Mid-cycle thresholds may include discrete resistance values, such as 5 MΩ or 3 MΩ, for example. When the end of cycle threshold is reached 96, typically around 1.5 MΩ, cycle PM parameters are reported 101, abnormal event filters and active zone algorithms are disabled 119, and sensor regen 48 initiated. Each of the above-mentioned reported parameters are tracked for the duration of the drive cycle 105 and reported periodically. Cumulative drive cycle totals are reset to zero 122 when ignition is turned off 120 before the controller powers down 121. The cumulative drive cycle totals may be used to more directly determine the efficiency of the diesel particulate filter 16. Previously DPF efficiency could only be inferred based upon measuring the entire cycle time.

Along with the corrected signal 58 that is delivered by the large particle filter 56, a rejected large particle signal amplitude 83 is made available to a large particle mass estimation algorithm 84. The mass each large particle is added to a cumulative large particle mass variable that is retained throughout the sensor cycle, and made available 113 to the other PM measurement algorithms described below.

Figure 10B:
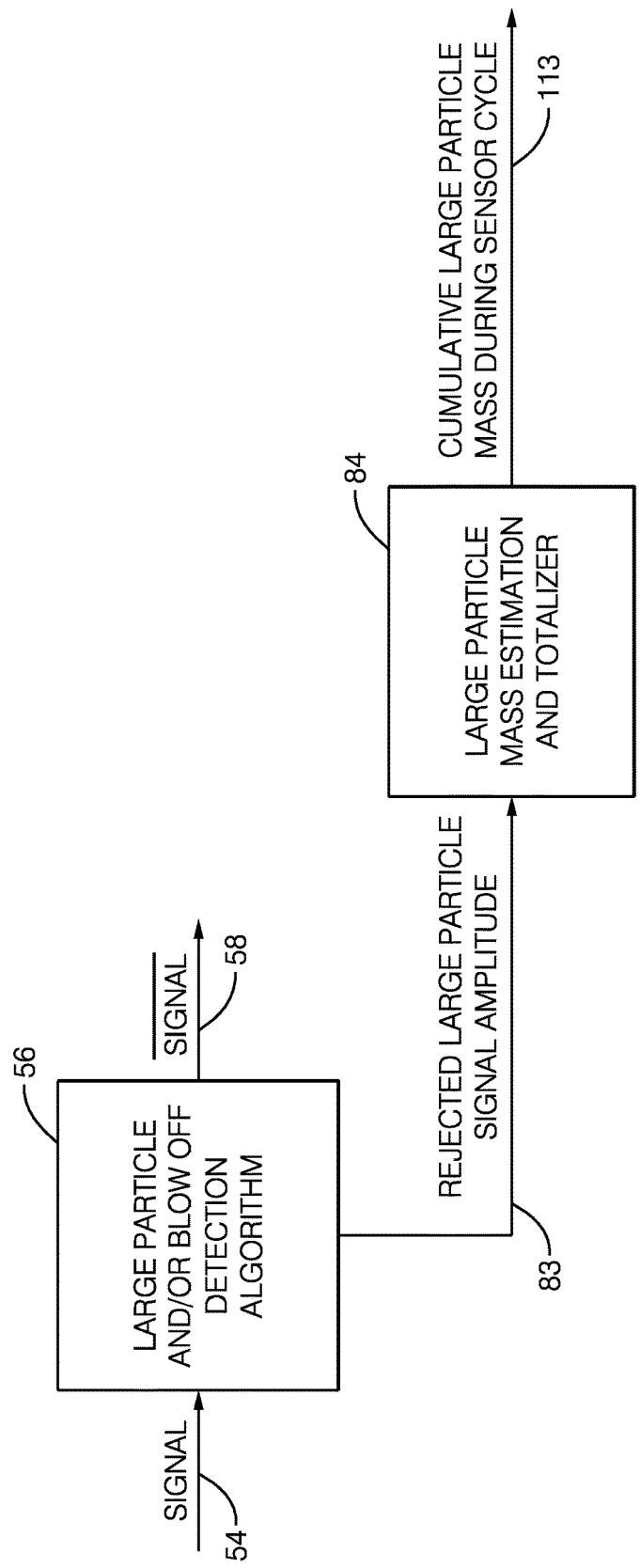
FIG. 10B schematically depicts the use of the rejected signal from the correction method in FIG. 10 to determine the mass of a large particle.

Typical PM measurement systems make no corrections for large particle or blow-off conditions. According to one aspect of this disclosure, it is possible to detect large particle strikes and blow-offs using the detection methods described above and generate a disturbance free signal 58. This signal is inherently compensated for blow-offs since they represent PM mass that existed on the sensor for some period of time, but then left the sensor electrodes. Large particles, on the other hand, have been removed from the disturbance-free signal and therefore their mass is unaccounted for. FIG. 10B provides a method in which each large particle is sized and added to a cumulative mass value for use when reporting total mass in subsequent algorithms. Referring now to FIG. 10B, the large particle filter 56 evaluates signal 54 to find and remove anomalies to generate corrected signal 58. The large particle filter also quantifies the amplitude of the large particle disturbance that is being rejected 83. The amplitude of this disturbance is correlated with the size of the particle which created the disturbance and method 84 determines the size of each large particle and adds its mass to a totalizer to track cumulative large particle mass 113 up to that point in the sensor cycle. This large particle mass is utilized by subsequent methods as described in FIGS. 11A-E.

FIGS. 11A-11E describe the use of corrected signal to extract information about PM mass, flux and concentration at various points in the sensor cycle and vehicle drive cycle. With the disclosed method shown in FIG. 5, deadband time can now be used to generate PM mass, average concentration, and average flux outputs at the end of the deadband period as described in FIG. 11A. Signal 58 and timer data 94 (which exists internally in controller 22) along with a deadband threshold calibration 90 is used to generate a deadband flag 92 and deadband time 93. The deadband time is used along with exhaust temperature 15, velocity 17 and pipe area 19 to determine (59) PM mass, average flux, and average concentration during the deadband period. These outputs 88 can be made available 89 to the ECU at the end of deadband. Evaluation of DPF performance can be made using these outputs, allowing a diagnostic decision to be made 25% to 50% sooner than the typical method, which relied upon the response time measurement approach previously described.

In operation, according to one example embodiment, the PM sensor 20 outputs a resistance at the conclusion of the deadband zone (point 50). This resistance measurement can be correlated to cumulative PM mass flux (mg/m$^2$) using a look-up table that is determined empirically. For example, the time may be measured from point 49 to point 50, which corresponds to a threshold resistance, e.g., 8 MΩ for one type of PM sensor 20. This deadband time corresponds to the cumulative soot flux, which is compensated using the exhaust gas temperature (T) and velocity. Average soot flux for the deadband zone can then be calculated as well as average soot concentration, and total soot mass using the exhaust gas velocity (V) and cross-sectional area (A), as shown below.

Average Soot Concentration (mg/m$^3$)=Deadband Cumulative Soot Flux (mg/m$^2$)/(deadband time (s)*Avg. Velocity (m/s))

Total Soot Mass (mg)=Deadband Cumulative Soot Flux (mg/m$^2$)*Cross-sectional Area (m$^2$)

Avg. Soot Flux (mg/m$^2$*s)=Deadband Cumulative Soot Flux (mg/m$^2$)/Deadband time (s)

Figure 11A:
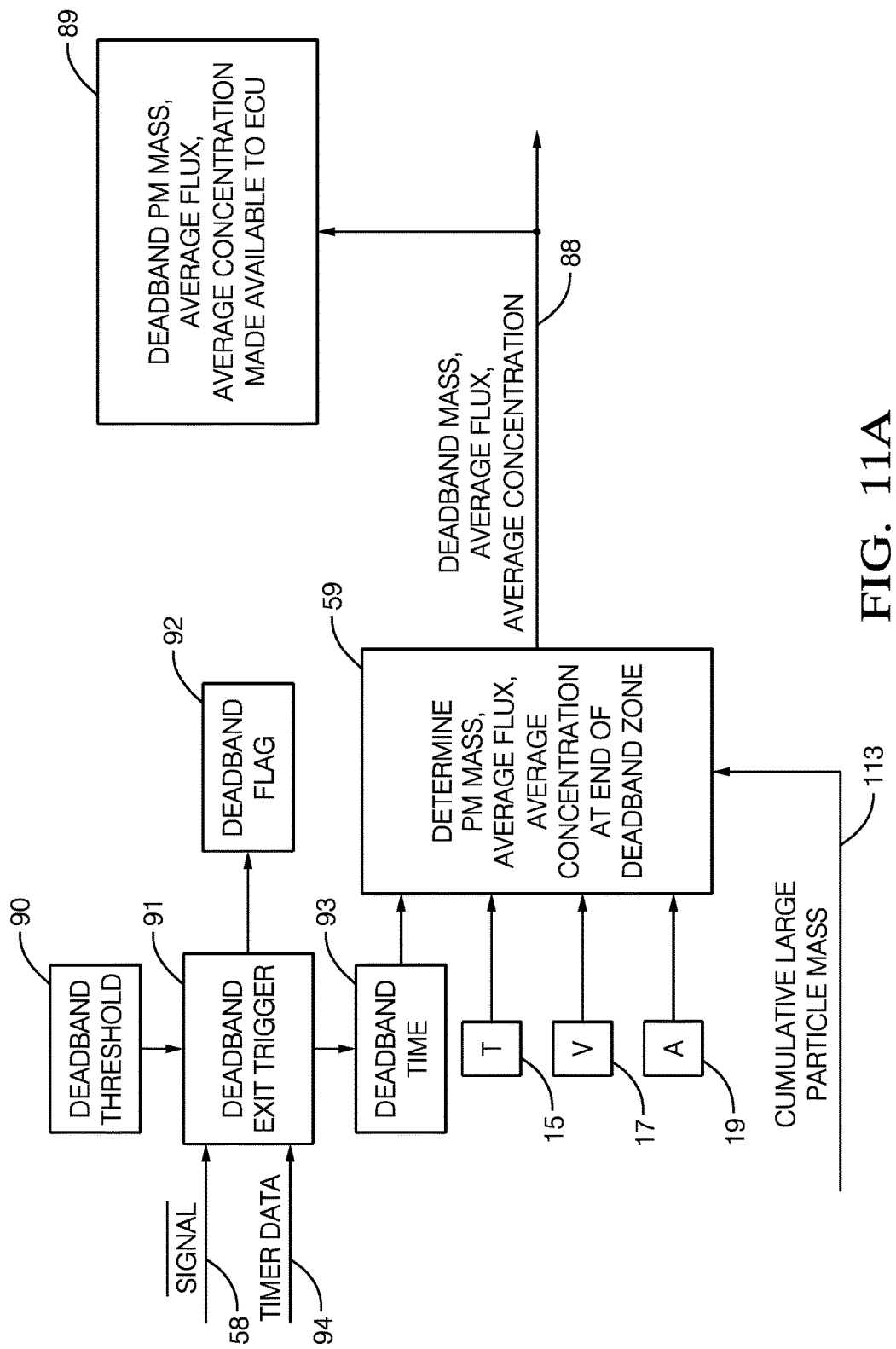
FIG. 11A schematically depicts the use of the corrected signal to determine PM mass, average flux, and average concentration at the end of the deadband zone of the current sensor cycle.
Figure 11B:
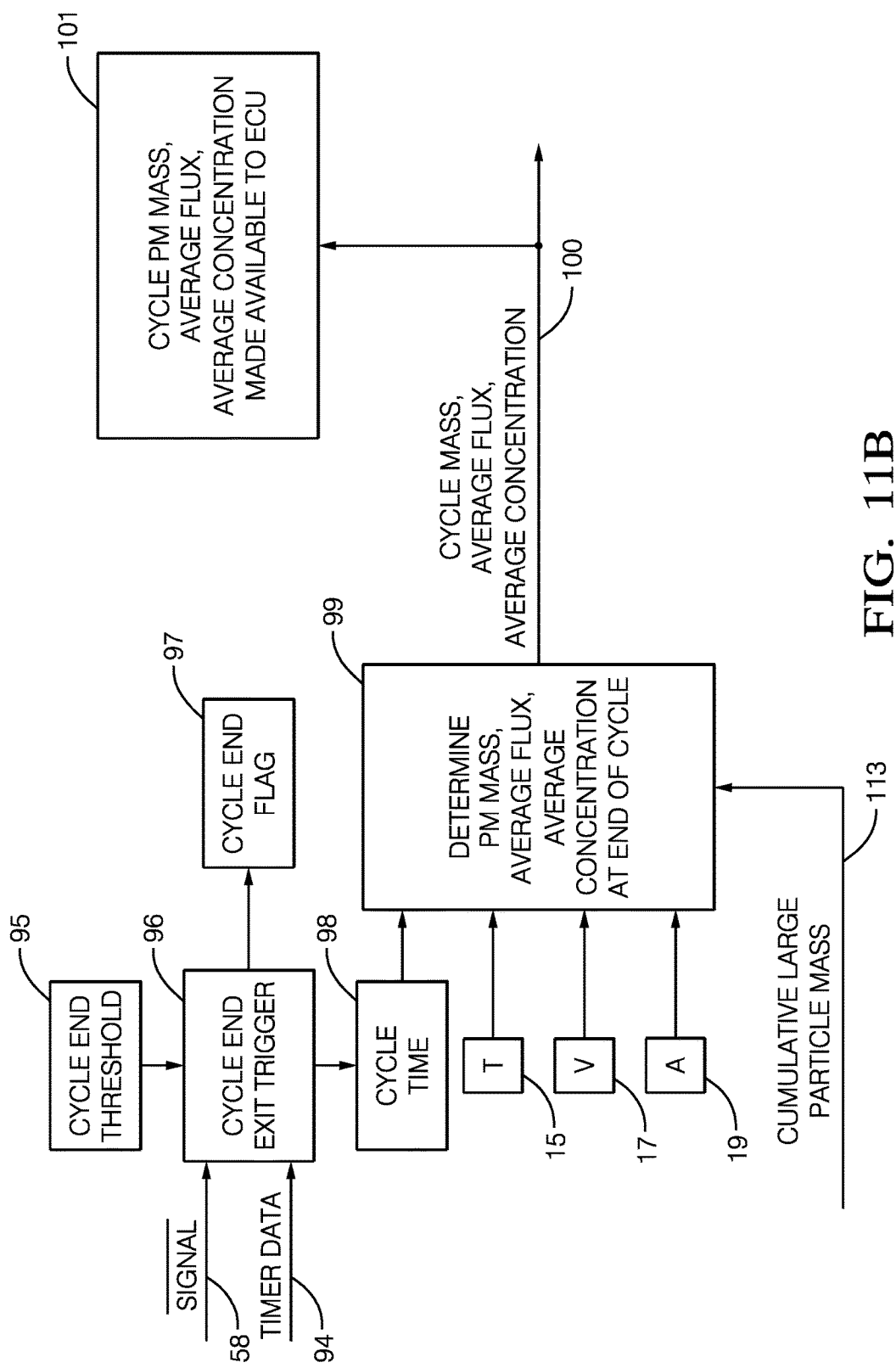
FIG. 11B schematically depicts the use of the corrected signal to determine PM mass, average flux, and average concentration at the end of the sensor cycle.

Referring to FIG. 11B, similar calculations can be made at the end of the active zone 52 using the cycle time 98 which is defined as the time between start of deadband 49 and end of active zone 52, as shown below. Again referring to FIG. 11b, the signal 58 is compared to the cycle end threshold 95 by an end of cycle trigger 96 to generate an end of cycle flag 97 and a cycle time 98. The cycle time is used along with exhaust temperature 15, velocity 17 and pipe area 19 to determine (99) PM mass, average flux, and average concentration during the sensor measurement cycle. These outputs 100 can be made available 101 to the ECU at the end of cycle. End of cycle calculations are shown below.

Average Soot Concentration (mg/m$^3$)=Cycle Cumulative Soot Flux (mg/m$^2$)/(cycle time (s)*Avg. Velocity (m/s))

Total Soot Mass (mg)=Cycle Cumulative Soot Flux (mg/m$^2$)*Cross-sectional Area (m$^2$)

Avg. Soot Flux (mg/m$^2$*s)=Cycle Cumulative Soot Flux (mg/m$^2$)/cycle time (s)

Figure 11C:
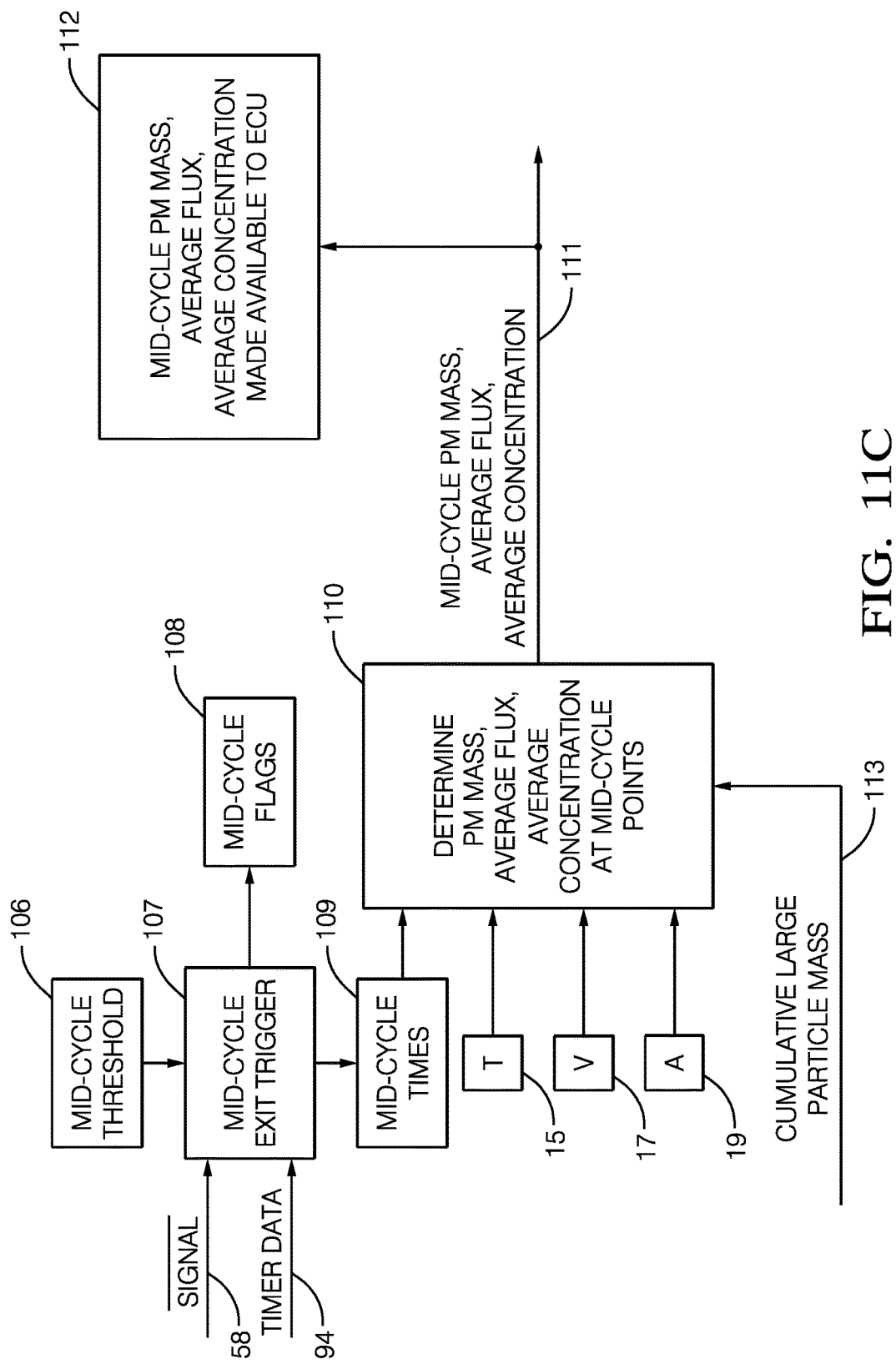
FIG. 11C schematically depicts the use of the corrected signal to determine PM mass, average flux, and average concentration at mid-cycle points of the current sensor cycle.

Furthermore, referring now to FIG. 11C, similar calculations can also be made at arbitrarily designated points (based on sensor resistance thresholds 106) within the active zone 46, using mid-cycle triggers 107, creating mid-cycle flags 108 and mid-cycle times 109 so that multiple determinations 110 of the average soot concentration, mass and flux can be provided throughout the active zone portion of the sensor cycle. These outputs 111 can be made available 112 to the ECU at the various points throughout the cycle. Mid-cycle calculations are shown below. This data can also be used to report end of PM cycle information if the cycle is terminated early for any reason including a detected instability in the accumulated soot.

Average Soot Concentration (mg/m$^3$)=Mid-Cycle Cumulative Soot Flux (mg/m$^2$)/(Mid-cycle time (s)*Avg. Velocity (m/s))

Total Soot Mass (mg)=Mid-Cycle Cumulative Soot Flux (mg/m$^2$)*Cross-sectional Area (m$^2$)

Avg. Soot Flux (mg/m$^2$*s)=Mid-Cycle Cumulative Soot Flux (mg/m$^2$)/Mid-cycle time (s)

Figure 11D:
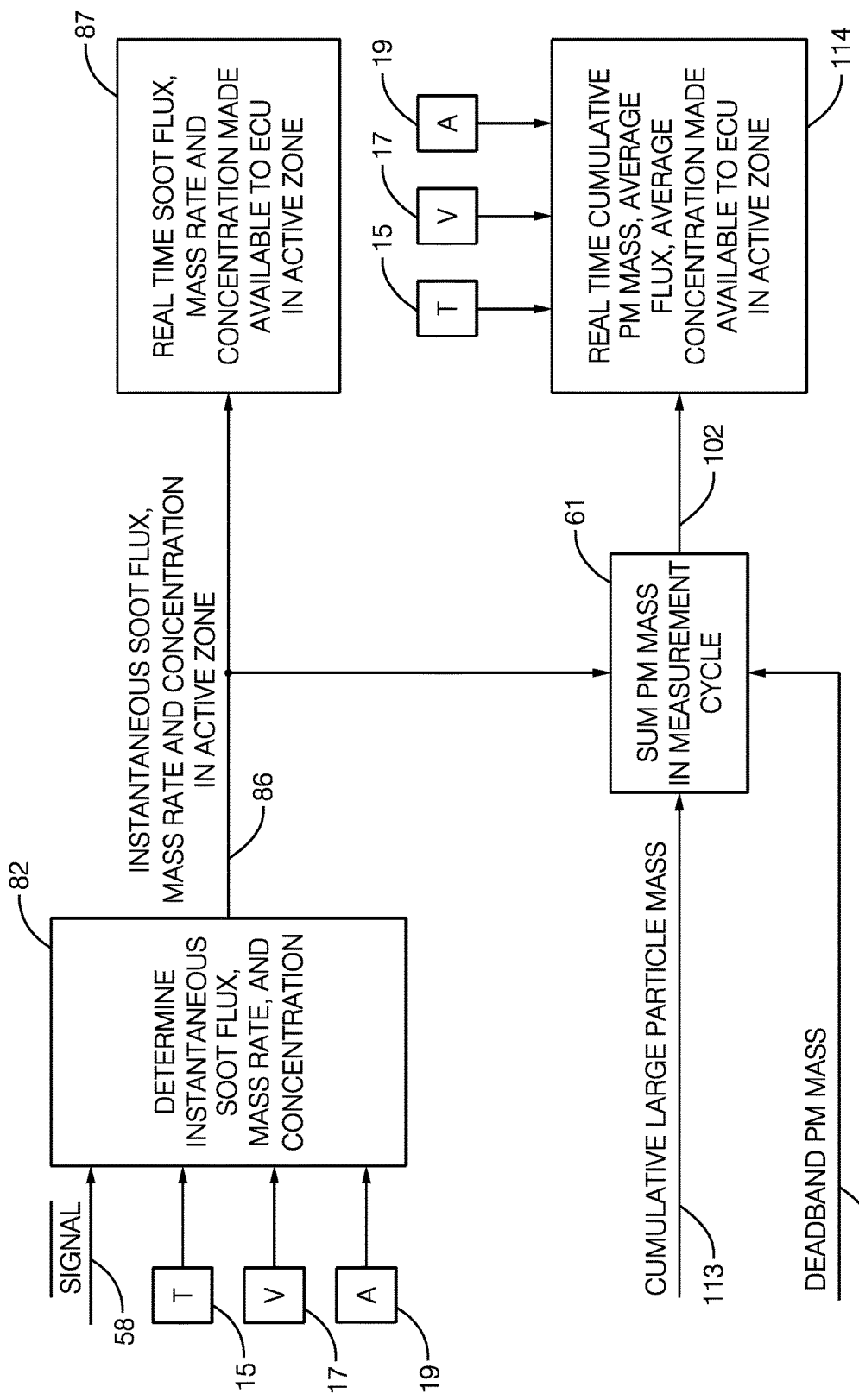
FIG. 11D schematically depicts the use of the corrected signal to determine instantaneous real-time PM mass rate, flux, and concentration along with cumulative PM mass, average flux and average concentration during the active zone of the current sensor cycle.
Figure 11E:
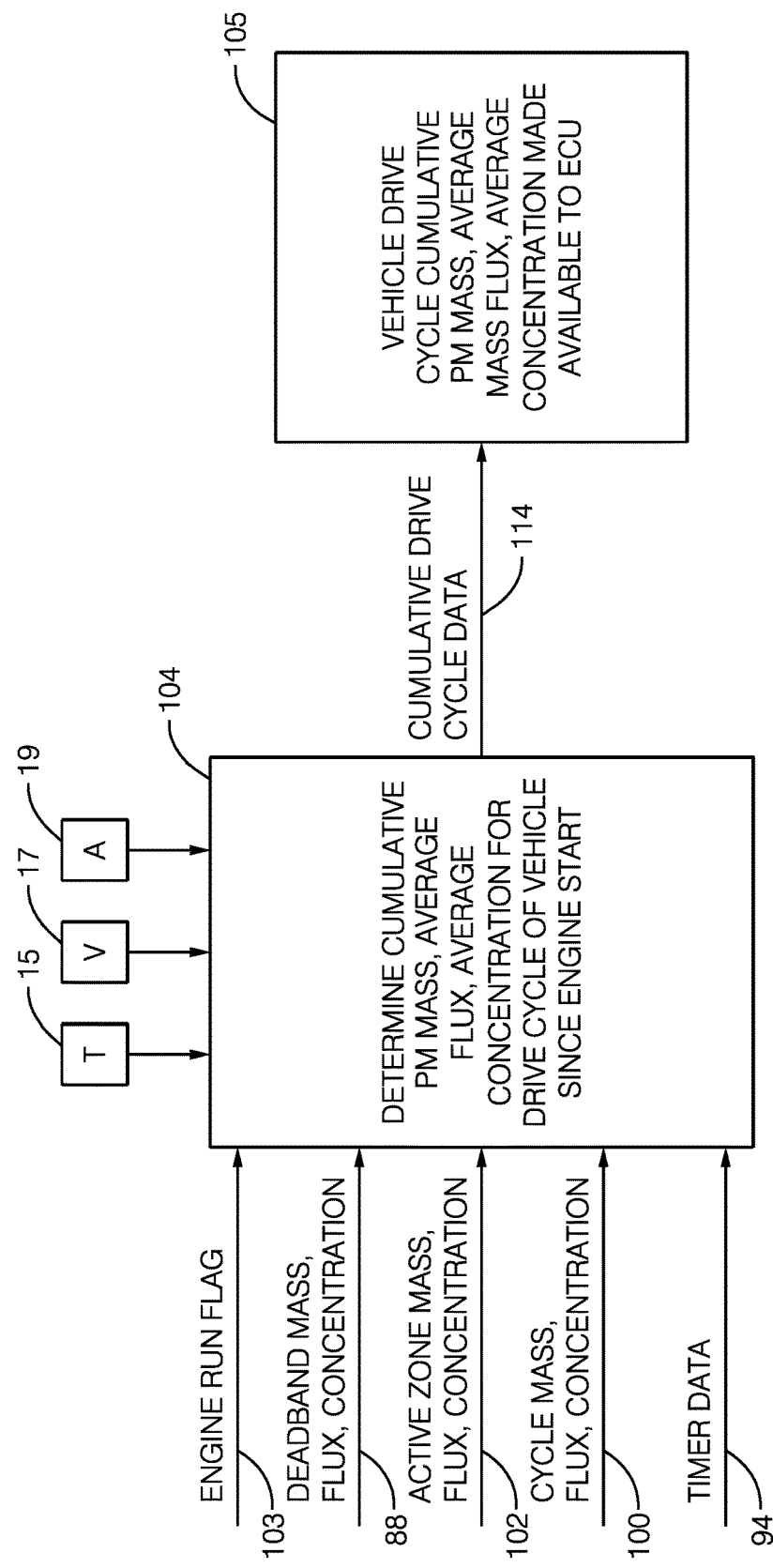
FIG. 11E schematically depicts the use of the aforementioned signals in FIGS. 11A-11D to determine cumulative vehicle drive cycle PM mass, average flux, and average concentration of the current vehicle drive cycle.

FIG. 11D describes a method which provides real-time instantaneous soot flux, mass rate, and concentration while the sensor is operating in the active zone. Corrected signal 58 is used to determine an instantaneous PM mass flux using the equation below.

In active zone 46, according to the disclosed embodiment, the sensor measurement controller 23 determines the soot flux rate by using the equation:

$$\text{soot flux} = k \frac{d^2G}{dt^2}$$

The constant, k, is an exhaust gas velocity-dependent constant that is empirically determined. This second derivative of the conductance, G, which is the inverse of the resistance, R, provides the PM mass flux (mg/m$^2$s), mass rate (mg/s) and real-time concentration (mg/m$^3$) 82, using exhaust velocity and the exhaust pipe cross-sectional area as described in more detail below. This second order response occurs only in the active zone, the response is first order before and after the active zone. The instantaneous mass flux, mass rate, and concentration data can be made available 87 to the ECU on a real-time basis. The corrected particulate matter accumulation rate calculation from the active zone (signal 86 in FIG. 11D) is added to the PM mass determination from the deadband zone 88 (block 89), along with the estimated cumulative large particle mass 113 (block 84) to provide the cumulative real-time particulate mass up to that point in the measurement cycle (block 61). This sum can be continually updated at regular time intervals so that continuous particulate mass accumulation data is readily available to the ECU through the remaining duration of the cycle. With additional calculations, a measure of the cumulative soot mass or soot concentration are made available 114 to the ECU using exhaust velocity and the exhaust pipe cross-sectional area. In this manner, total accumulated particulate matter can be determined and then used for sensor regeneration and/or engine/vehicle testing and diagnostic procedures.

Real-time Cumulative Soot Mass in active zone (mg)=Deadband mass (mg)+Integral of real-time active zone mass (mg)

Real-time Avg. Soot Flux in active zone (mg/m$^2$*s) =Running average of instantaneous soot flux in active zone (mg/m$^2$*s)

Real-time Avg. Soot Concentration in active zone (mg/m$^3$)=Real-time Avg. Soot Flux (mg/m$^2$)/ (Active zone time (s)*Avg. Active Zone Velocity (m/s))

Cumulative drive cycle information can be obtained by combining the above mentioned PM flux, mass and concentration information collected during the deadband 88, active zone 102, and end of cycle 100 along with the timer data 94, temperature 15, velocity 17, and pipe area 19 data and an engine run flag 103 from the ECU. Using this information, a determination can be made 104 regarding the cumulative PM mass, average flux and average concentration for the current vehicle drive cycle since engine start. This information 114 can then be made available 105 to the ECU. Data from the previous sensor cycle 100 can be used to generate an estimate of the ongoing soot mass rate, flux and concentration using extrapolation of the system performance from the most recent performance data from the active zone 102 to predict system performance in the current sensor deadband zone. Once the sensor exits deadband, the current cycle deadband data 88 is used to correct the estimate that was based on the previous cycle. Data from the current active zone 102 is then used to keep the drive cycle data 114 updated to the current real-time status. At the end of the sensor cycle, cycle data 100 can be used to fine tune data drive cycle data generated during the active zone. Equations used are identical to those listed above with the exception that cumulative values and timers do not reset to zero at each sensor end of cycle.

The controllers, for example, controllers 21-24, which may be integrated with one another or separate, may include a processor and non-transitory memory where computer readable code for controlling operation is stored. In terms of hardware architecture, such a controller can include a processor, memory, and one or more input and/or output (I/O) device interface(s) that are communicatively coupled via a local interface. The local interface can include, for example but not limited to, one or more buses and/or other wired or wireless connections. The local interface may have additional elements, which are omitted for simplicity, such as controllers, buffers (caches), drivers, repeaters, and receivers to enable communications. Further, the local interface may include address, control, and/or data connections to enable appropriate communications among the aforementioned components.

The controllers may be a hardware device for executing software, particularly software stored in memory. The processor can be a custom made or commercially available processor, a central processing unit (CPU), an auxiliary processor among several processors associated with the controller, a semiconductor based microprocessor (in the form of a microchip or chip set) or generally any device for executing software instructions.

The memory can include any one or combination of volatile memory elements (e.g., random access memory (RAM, such as DRAM, SRAM, SDRAM, VRAM, etc.)) and/or nonvolatile memory elements (e.g., ROM, etc.). Moreover, the memory may incorporate electronic, magnetic, optical, and/or other types of storage media. The memory can also have a distributed architecture, where various components are situated remotely from one another, but can be accessed by the controller.

The software in the memory may include one or more separate programs, each of which includes an ordered listing of executable instructions for implementing logical functions. A system component embodied as software may also be construed as a source program, executable program (object code), script, or any other entity comprising a set of instructions to be performed. When constructed as a source program, the program is translated via a compiler, assembler, interpreter, or the like, which may or may not be included within the memory.

The input/output devices that may be coupled to system I/O Interface(s) may include input devices, for example, but not limited to, a scanner, microphone, camera, proximity device, etc. Further, the input/output devices may also include output devices, for example but not limited to a display, etc. Finally, the input/output devices may further include devices that communicate both as inputs and outputs, for instance but not limited to, a modulator/demodulator (for accessing another device, system, or network), a radio frequency (RF) or other transceiver, a bridge, a router, etc.

When the controller is in operation, the processor can be configured to execute software stored within the memory, to communicate data to and from the memory, and to generally control operations of the computing device pursuant to the software. Software in memory, in whole or in part, is read by the processor, perhaps buffered within the processor, and then executed.

It should be understood that although particular step sequences are shown, described, and claimed, the steps may be performed in any order, separated or combined unless otherwise indicated and will still benefit from the present invention.

Although the different examples have specific components shown in the illustrations, embodiments of this invention are not limited to those particular combinations. It is possible to use some of the components or features from one of the examples in combination with features or components from another one of the examples.

Furthermore, although an example embodiment has been disclosed, a worker of ordinary skill in this art would recognize that certain modifications would come within the scope of the claims. For that reason, the following claims should be studied to determine their true scope and content.

What is claimed is:

1. A method of quantifying a particulate matter in an exhaust stream comprising the steps of:
   accumulating a particulate matter on a sensor, wherein the sensor provides a signal that varies based upon an amount of the particulate on the sensor, wherein the sensor includes a measurement cycle that includes a deadband zone, followed by an active zone, which is followed by a regeneration zone; and
   calculating the particulate matter after an end of the deadband zone is reached and prior to an end of the measurement cycle;
   wherein the particulate matter calculating step includes determining at least one of a particulate matter mass, a particulate matter flux, and a particulate matter concentration;
   wherein the particulate matter calculating step includes determining at least one of an average amount and an instantaneous amount of the at least one of the particulate matter mass, the particulate matter flux, and the particulate matter concentration; and
   wherein the instantaneous amount of the at least one of the particulate matter mass, the particulate matter flux, and the particulate matter concentration is calculated using a second differential of conductance from the signal.

2. The method according to claim 1, wherein the particulate matter calculating step is performed at an end of the active zone.

3. The method according to claim 1, wherein the particulate matter calculating step is performed within the active zone.

4. The method according to claim 3, wherein the particulate matter calculating step is performed when the signal reaches a desired resistance.

5. The method according to claim 3, comprising the step of reporting the calculated particulate matter if the measurement cycle is terminated prematurely.

6. The method according to claim 1, comprising an exhaust system fluidly connected to an engine, the exhaust system defines the exhaust stream, the sensor includes a heater and is provided in the exhaust system, and comprising the step of energizing the heater in the regeneration zone.

7. The method according to claim 1, comprising the step of calculating a cumulative particulate matter during a vehicle drive cycle.

8. A method of quantifying a particulate matter in an exhaust stream comprising the steps of:
   accumulating a particulate matter on a sensor, wherein the sensor provides a signal that varies based upon an amount of the particulate on the sensor, wherein the sensor includes a measurement cycle that includes a deadband zone, followed by an active zone, which is followed by a regeneration zone; and
   calculating the particulate matter after an end of the deadband zone is reached and prior to an end of the measurement cycle;
   calculating a particulate matter in the deadband zone based upon the signal reaching a threshold resistance and a deadband zone total time at which the threshold resistance is reached from an end of the regeneration zone, and the step of summing a particulate matter from the deadband zone and the active zone to determine a total accumulated particulate matter during the measurement cycle.

9. A method of quantifying a particulate matter in an exhaust stream comprising the steps of:
   accumulating a particulate matter on a sensor, wherein the sensor provides a signal that varies based upon an amount of the particulate on the sensor, wherein the sensor includes a measurement cycle that includes a deadband zone, followed by an active zone, which is followed by a regeneration zone; and
   calculating the particulate matter in the deadband zone based upon the signal reaching a threshold resistance and a deadband zone total time at which the threshold resistance is reached from an end of the regeneration zone.

10. The method according to claim 9, wherein the particulate matter calculating step includes determining at least one of an average particulate matter mass, an average particulate matter flux, and an average particulate matter concentration.

11. The method according to claim 9, comprising the step of outputting a diesel particulate filter status message based upon the deadband zone total time exceeding a threshold.

12. A system comprising:
   an exhaust system fluidly configured to define an exhaust stream;
   a sensor arranged in the exhaust system and configured to be exposed to the exhaust stream and accumulate a particulate matter on the sensor, wherein the sensor provides a signal that varies based upon an amount of the particulate matter on the sensor, wherein the sensor is configured to provide a measurement cycle that includes a deadband zone, followed by an active zone, which is followed by a regeneration zone; and a control system in communication with sensor, control system includes a controller configured to calculate at least one of:

the particulate matter after an end of the deadband zone is reached and prior to an end of the measurement cycle; and the particulate matter in the deadband zone based upon the signal reaching a threshold resistance and a deadband zone total time at which the threshold resistance is reached from an end of the regeneration zone.

13. The system according to claim 12, wherein the controller is configured to determine at least one of a particulate matter mass, a particulate matter flux, and a particulate matter concentration when calculating the particulate matter.

14. The system according to claim 12, wherein the controller is configured to report the calculated particulate matter if the measurement cycle is terminated prematurely.

15. The system according to claim 12, comprising an exhaust system fluidly connected to an engine, the exhaust system defines the exhaust stream, the sensor includes a heater and is provided in the exhaust system, and wherein the controller is configured to energize the heater in the regeneration zone in response to the calculated particulate matter.

16. The system according to claim 12, wherein the controller is configured to calculate a cumulative particulate matter during a vehicle drive cycle.

* * * * *